United States Patent [19]

Baroody et al.

[11] Patent Number: 5,256,220
[45] Date of Patent: Oct. 26, 1993

[54] LIQUID MONOPROPELLANTS

[75] Inventors: Edward E. Baroody, Bryans Rd.; Horst G. Adolph, Silver Spring; Mortimer J. Kamlet, Rockville; Robert C. Gill, White Plains; Herman S. Haiss, Forest Heights, all of Md.

[73] Assignee: The United States of America as represented by the Secretary of the Navy, Washington, D.C.

[21] Appl. No.: 101,402

[22] Filed: Dec. 3, 1979

[51] Int. Cl.$^5$ .............................. C06B 25/00
[52] U.S. Cl. ........................... 149/88; 149/92
[58] Field of Search .................... 149/88, 92

[56] References Cited

U.S. PATENT DOCUMENTS

| | | | |
|---|---|---|---|
| 3,116,188 | 12/1963 | Austin | 149/88 |
| 3,387,033 | 6/1968 | Talbott et al. | 260/583 |
| 3,432,554 | 3/1969 | Peters et al. | 260/583 |
| 3,479,404 | 11/1969 | Smith et al. | 260/583 |
| 3,484,486 | 12/1969 | Grigor et al. | 260/563 |
| 3,629,338 | 12/1971 | Martin | 149/88 X |
| 3,631,155 | 12/1971 | Smiley | 260/453 |
| 3,634,158 | 1/1972 | Camp | 149/88 |
| 3,700,393 | 10/1972 | Mueller | 60/214 |
| 3,700,723 | 10/1972 | Coon et al. | 149/88 X |
| 3,705,197 | 12/1972 | Kaplan et al. | 149/88 X |
| 3,751,476 | 8/1973 | Adolph et al. | 149/92 X |
| 3,770,795 | 11/1973 | White | 149/88 X |
| 3,778,319 | 12/1973 | Benziger | 149/92 X |
| 3,845,104 | 10/1974 | Gilligan | 149/92 X |
| 3,845,105 | 10/1974 | Gilligan | 149/92 X |
| 3,873,617 | 3/1975 | Adolph et al. | 149/92 X |
| 3,907,907 | 9/1975 | Frankel et al. | 149/92 X |
| 3,962,349 | 6/1976 | Adolph | 149/88 X |
| 4,026,739 | 5/1977 | Reitlinger | 149/88 |
| 4,048,219 | 9/1977 | Adolph | 560/156 |
| 4,214,929 | 7/1980 | Camp et al. | 149/88 |
| 4,219,374 | 8/1980 | Cziesla et al. | 149/75 |
| 4,292,098 | 9/1981 | Mastroianni et al. | 149/88 |
| 4,764,231 | 8/1988 | Slawinski et al. | 149/88 |
| 4,988,397 | 1/1991 | Adolph et al. | 149/88 |

*Primary Examiner*—Edward A. Miller
*Attorney, Agent, or Firm*—John D. Lewis

[57] ABSTRACT

A novel formulation of liquid propellants comprising a mixture of high energy ingredients consisting of bis(2-fluoro-2,2-dinitroethyl)amine, bis(2-fluoro-2,2-dinitroethyl)formal and bis(2,2,2-trinitroethyl)formal together with conventional liquid fuels and propellants to create a synergistic formulation having new and unexpected physical and chemical properties.

8 Claims, No Drawings

LIQUID MONOPROPELLANTS

BACKGROUND OF THE INVENTION

It is well known and conventional to use Otto fuels and other liquid fuels to propel torpedoes and other solid projectiles.

It is likewise common in the liquid propellant art to utilize liquid propellants for guns as well as for rocket fuel.

There are a number of typical problems with these prior art fuels and liquid propellants including low impetus, high flame temperatures and poor gas production per unit mass of fuel.

Other liquid fuels and propellants are very sensitive to shock and present safety problems. Most safety problems with liquid propellants are caused by the sensitivity to temperature and pressure of the material involved.

It is further well known in the art that some liquid propellants are extremely sensitive to shock. In addition many conventional explosives and propellants lack sufficient thermal stability for use in high temperature environments.

Conventional liquid propellants are less stable and more sensitive to shock than the formulations made according to the instant invention.

In the Otto Fuel and Otto Fuel II formulations that are presently used by the navy as torpedo propellants there are drawbacks, primarily because these fuels are extremely corrosive and present health hazards if leakage is allowed to occur. The fumes from Otto Fuel II are extremely toxic to personnel in the area.

Accordingly, it is one object of the invention to formulate liquid propellants, that can be easily formulated and manufactured in commercial quantities.

It is also a primary object to provide Otto Fuel II formulations that combine better performance characteristics with lower toxicity.

It is another object of the present invention to formulate novel mixtures and compositions of liquid propellants that have improved physical and chemical properties.

It is a further object of this invention to incorporate and utilize several high energy ingredients in a number of conventional liquid fuels and propellants, to improve the energetic characteristics of the liquid propellants.

It is another object of this invention to formulate liquid propellants that have superior thermodynamic properties and characteristics that give new and unexpected results.

It is a further object to formulate novel propellants and other similar materials including liquid propellants so as to yield improved safety characteristics.

It is still a further object of this invention to formulate novel mixtures of liquid propellants with better DTA curves, improved test data and oven times and better auto-ignition times when compared with conventional propellant materials.

It is a still further object of this invention to formulate torpedo propellants by increasing energetic properties while decreasing toxicity.

It is another object of this invention to prepare formulations that are less hazardous to personnel who are in close proximity to said Otto Fuel formulations.

It is a still further object of this invention to formulate liquid fuels and propellants that have greatly superior cavity drop test results.

It is another object of this invention to prepare and use formulations of liquid propellants that have greatly lessened sensitivity to shock.

It is another object of this invention to produce formulations of liquid propellants that have greatly increased impetus (foot, pounds per pound) while being combined with a lower flame temperature).

SUMMARY OF THE INVENTION

The invention comprises the product of formulation of a high energy ingredient mixed together with conventional liquid fuels and propellants. The formulated product yields new and unexpected results. The high energy ingredient is a compound usually selected from the group consisting of bis(2-fluoro-2,2-dinitroethyl)amine, bis(2-fluoro-2,2-dinitroethyl)formal, and bis(2,2,2-trinitroethyl)formal. Equivalent compounds selected from Table 1 may be substituted for these components, although the results may not be the same as with each compound but will prove satisfactory.

In most cases the high energy ingredient is present in an amount varying between 5% and 75% of the total mixture.

In general, the use of a compound selected from the group consisting of bis(2-fluoro-2,2-dinitroethyl)amine, bis(2-fluoro-2,2-dinitroethyl)formal, and bis(2,2,2-trinitroethyl)formal, when mixed with well-known liquid fuels and propellants, will yield a formulated product that will have physical and chemical properties that are superior to either the high energy ingredient or the conventional fuels and propellants.

PREFERRED EMBODIMENT

There are several preferred embodiments of the invention. The operative compounds are set forth and disclosed in Table I together with some energy factors.

In one preferred embodiment, Otto Fuel, a well known liquid propellant used by the U. S. Navy for torpedo propulsion can be formulated with one or more compounds selected from the group consisting of bis(2-fluoro-2,2-dinitroethyl)amine, bis(2,-fluoro-2,2-dinitroethyl)formal and bis(2,2,2-trinitroethyl)formal.

TABLE I

Illustrations of the High Energy Ingredient that may be used in the Preferred Embodiment Formulations

| Abbrev. | Name | $H_f$ 298.15° K. K cal/mole |
|---------|------|---------------------------|
| FEFO | Bis(2-fluoro-2,2-dinitroethyl)formal | −179.8 |
| BFDNA | Bis(2-fluoro-2,2-dinitroethyl)amine | −126.95 |
| TEFO | Bis(2,2,2-trinitroethyl)formal | −96.40 |

The resulting product of the formulation has much higher impetus than Otto Fuel II alone while increasing burning rates and combustion properties. In each instance where the high energy ingredient is used in the range of from 5 to 75% by weight of the mixture, toxicity of Otto Fuel II is decreased significantly.

The experimental data illustrating the results of the combination of bis(2,2,-trinitroethyl)formal, hereinafter referred to as TEFO is set forth in Tables II, III, IV, V, VI, VII and VIII. In another preferred embodiment, diethyl oxalate is formulated with a compound selected from the group consisting of bis(2-fluoro-2,2-dinitroethyl)amine, bis(2-fluoro-2,2-dinitroethyl)formal and bis(2,2,2-trinitroethyl)formal. This experimental data best illustrates the combination of mixing TEFO with diethyl oxalate and is set forth in Tables V, VI, and VII.

In another preferred embodiment a compound selected from the group consisting of bis(2-fluoro-2,2-dinitroethyl)amine, bis(2-fluoro-2,2-dinitroethyl)formal and bis(2,2,2-trinitroethyl)formal is mixed with acetone and methylethyl ketone. The experimental data illustrating the results of the combination of TEFO, acetone and methylethyl ketone is set forth in Table VIII.

High Energy Ingredients Formulated With Otto Fuel II

Otto Fuel II is a liquid fuel that is now used extensively by the U.S. Navy to propel torpedoes.

Surprisingly, it has been found that formulation of one or more of the high energy ingredients selected from Table I when mixed with Otto Fuel II will yield high energy propellants having new and unexpected properties.

Preparation and Testing of Otto Fuel II

Otto Fuel II is comprised of 2-nitrodiphenylamine prepared in accordance with MIL-N-3399; di-n-butyl sebacate; prepared to conform with DOD-B-82669; and propylene glycol dinitrate that is prepared to conform with the requirements of DOD-P-82671.

The chemical composition of Otto Fuel II is: A mixture of propylene glycol dinitrate, 2-nitrodiphenylamine, di-n-butyl sebacate.

| CHEMICAL COMPOSITION OF OTTO FUEL II | | | |
|---|---|---|---|
| Component | Minimum (% by wt) | Maximum (% by wt) | Test method |
| Propylene glycol dinitrate | 75.8 | 76.2 | 4.5.2.1 |
| 2-Nitrodiphenylamine | 1.4 | 1.6 | 4.5.2.2 |
| Di-n-butyl sebacate | 22.2 | 22.8 | 4.5.2.3 |
| Sodium | — | 0.8 | 4.5.2.5 |

The detailed method of testing the propylene glycol dinitrate for content and quality is set forth in Metail in MIL-O-82652(OS), pages 4 and 5.

The detailed method of testing the #2nitrodiphenylamine for content and quality is set forth in detail in MIL-O-82652(OS), pages 5, 6 and 7.

The detailed method of testing the di-n-butyl sebacate content and quality is set forth in MIL-0-82672(OS), pages 7 and 8.

The detailed method of testing the sodium content and quality set forth in OD 43852 and on page 8 of MIL-O-82672(OS).

EXAMPLE 1

TEFO is prepared by first producing trinitroethanol. In a second step trinitroethanol is reacted with paraformaldehyde and the crude product is purified.

Typical Laboratory Preparation

1. Preparation of trinitroethanol (TNEOH):

The following ingredients were placed in a three-neck 250 ml flask equipped with a stirrer, thermometer, dropping funnel, and a bath for heating or cooling:

| | | |
|---|---|---|
| Aqueous nitroform (33.27% nitroform) = | 135.7 grams | (0.30 moles) |
| Carbon tetrachloride = | 63.4 grams | |
| methylene chloride = | 53.4 grams | |
| paraformaldehyde = | 10.4 grams | (0.33 moles) |

Sulfuric acid (51.5 g of 37.5% acid) was slowly added from the dropping funnel into the stirring mixture while maintaining temperature of 35° C. After a one hour reaction time, the mixture was separated into two layers, aqueous and organic, using a separatory funnel. Then the aqueous layer was extracted four times with methylene chloride (40.1 g portions) and discarded. The organic layer, containing most of the TNEO was combined with the extracts and the resulting mixture dried by azeotropic distillation. During this drying, the temperature of the solution was not allowed to exceed 50° C. A small portion of the dried TNEOH solution was used to determine the reaction yield. Vacuum removal of the diluent from the sample (14.6 g) at room temperature left 3.7g of the TNEOH (a white solid with melting point range of 58°-62° C). The TNEOH was formed in a 90% yield.

2. Preparation of TEFO:

Paraformaldehyde (3.9 g) was dissolved in reagent grade concentrated sulfuric acid (110.4 g of 96.5% $H_2SO_4$) and then slowly dripped into the well stirred TNEOH solution (44.9 g of TNEOH) prepared in the first step, above. The temperature was maintained at 20° to 25° C. and the stirring continued for one hour. After this time interval, the sulfuric acid layer and the organic layer were separated with the aid of a separatory funnel. The acid layer was extracted once with methylene chloride (66.5 g) and then discarded. Next the extract was combined with the organic layer. This combined solution was washed twice, four times, and three times with 50 ml each of, respectively, water, 3% aqueous sodium bicarbonate and water. After removal of the diluents by using a rotary evaporator and vacuum, an off-white solid remained. This solid, having a melting point range of 59°-61° C., was obtained in a 78% yield.

The crude product was purified by employing a precipitation technique. It was dissolved in ethanol (100 ml) and then precipitated by adding water (100 ml). Filtration and vacuum drying resulted in a 60% total yield of a white solid, which melted at 64° C.

The TEFO produced was mixed with conventional Otto Fuel II at room temperature, in the proportions by weight shown in Table II.

The The results shown in this table indicate the melting points of the TEFO - Otto Fuel II formulations.

The results in Table III indicate the heats of explosion of four (4) different formulations of TEFO and Otto Fuel II.

In the second section of Table III cavity drop tests results are indicated for four (4) different formulations of Otto Fuel II and TEFO.

The results in Table IV indicate the quality of gas (Moles/100 grs), Impetus (ft-lb/lb) and ISp (lb sec/lb) for 16 different formulations of TEFO and Otto Fuel II.

EXAMPLE 2

TEFO as prepared in Example 1 is mixed with conventional diethyl oxalate at room temperature. The results shown in Table V illustrate eight (8) different formulations of diethyl oxalate and TEFO.

The gas generated (moles/100 grams); impetus (ft-lb/lb) and Isp (lb-sec/lb) disclosed in Table V clearly indicate new and unexpected results in chemical and physical properties flowing from the formulation of Otto Fuel II with TEFO.

EXAMPLE 3

TEFO is mixed with a number of conventional solvents including diethyl oxalate, methyethyl ketone and acetone. The results, based upon eight (8) different formulations is set forth in Table VI. The results in Table VII indicate the thermodynamic and test data on TEFO, diethyl oxalate, methyl ethyl ketone and acetone.

EXAMPLE 4

TEFO, acetone, methylethyl ketone were mixed and tested. The experimental data is set forth in Table VIII.

The examples are only intended to be illustrative, since obvious modifications and equivalents in the invention will be evident to those skilled in the chemical arts, and propose to be bound solely by the appended claims.

TABLE II

Heats of Explosion, cavity drop Test, Density, and Melting Point-Data

|  | Density (grs/cc) |
|---|---|
| TEFO | 1.70 |
| BFDNA | 1.72 |

| Ingredients | | |
|---|---|---|
| TEFO | Otto-2 Fuel | Melting Points (°C.) |
| — | 100 | −36.5 |
| 10 | 90 | −39.5 |

TABLE II-continued

Heats of Explosion, cavity drop Test, Density, and Melting Point-Data

| 15 | 85 | −40.5 |
|---|---|---|
| 20 | 80 | −42.0 |
| 25 | 75 | −43.5 |
| 30 | 70 | −45.0 |
| 35 | 65 | −46.5 |
| 40 | 60 | −47.0 |

TABLE III

| Percent | | | Heats of Explosion |
|---|---|---|---|
| Otto-2 Fuel | TEFO | NOS 365 | $E_c$ (cal/gram) |
| 100 | — | — | −732.8 |
| 60 | 40 | — | 942.6 |
| 50 | 50 | — | −1083.5 |
| 40 | 60 | — | −1204.7 |
| — | — | 100 | 893.2 |

| Percent | | | Cavity Drop Test cm |
|---|---|---|---|
| Otto-II Fuel | TEFO | NO SET** | (2 kilogram weight used) |
| 100 | — | — | 18 |
| 40 | 60 | — | 10.4 |
| 50 | 50 | — | 3.4 |
| — | — | 100 | 6 to 7 |

NO SET (TEGDN = 96, Dibutylsebacate = 3% Ethyl (entralite = 1%)

|  | Density |
|---|---|
| BFDNA | 1.72 |
| TEFO | 1.70 |
| DITEFO | 1.83 |

TABLE IV

TEFO, Otto-2 Fuel Formulations

| Ingredient | | | | | | | | | |
|---|---|---|---|---|---|---|---|---|---|
| TEFO | — | 5 | 10 | 15 | 20 | 25 | 30 | 35 | 40 |
| Otto-II Fuel | 100 | 95 | 90 | 85 | 80 | 75 | 70 | 65 | 60 |
| Const. Vol. T. (°K.) | 2194 | 2251 | 2314 | 2383 | 2463 | 2556 | 2671 | 2813 | 2979 |
| Const. Press. T. (°K.)* | 1390 | 1434 | 1503 | 1615 | 1753 | 1901 | 2052 | 2234 | 2363 |
| Gas (moles/100 g) | 5.417 | 5.401 | 5.358 | 5.387 | 5.191 | 5.075 | 4.946 | 4.811 | 4.671 |
| (ft-lb/lb) | 330755 | 338408 | 345008 | 350703 | 355732 | 360995 | 367656 | 376618 | 38740 |
| ISP (lb-sec/lb) | 205.3 | 206.9 | 208.8 | 211.3 | 214.5 | 218.3 | 222.7 | 227.6 | 232.7 |

| TEFO | 45 | 50 | 55 | 60 | 65 | 70 | 75 |
|---|---|---|---|---|---|---|---|
| Otto-2 Fuel | 55 | 50 | 45 | 40 | 35 | 30 | 25 |
| Const. Vol. T. (°K.) | 3160 | 3347 | 3539 | — | 3120 | 3229 | 3307 |
| Const. Press. T. (°K.)* | 2522 | 2681 | 2838 | 2987 | — | — | — |
| Gas (moles/100 g) | 4.533 | 4.394 | 4.258 |  | 3.994 | 3.876 | 3.769 |
| (ft-lb/lb) | 3989599 | 409314 | 419327 |  |  |  |  |
| ISP (lb-sec/lb) | 237.7 | 242.5 | 247.0 | 251.2 | 255 | 258.4 | 261.1 |

*Constant pressure at 1000 psi

TABLE V

Diethyl Oxalate and TEFO Formulations

| Ingredient | | | | | |
|---|---|---|---|---|---|
| Diethyl Oxalate | 10 | 30 | 50 | 70 | 90 |
| TEFO | 90 | 70 | 50 | 30 | 10 |
| Const. Vol. T. (°K.)* | 4394 | 2866 | 1994 | 1664 | 1314 |
| Const. Pre. T. (°K.)** | 3326 | 2291 | 1283 | 1161 | 1010 |
| Gas (moles/100 grs) | 3.561 | 4.317 | 4.746 | 4.132 | 3.534 |
| IMPETUS (ft-lb/lb) | 446467 | 344124 | 268111 | 198720 | 126135 |
| Isp (lb-sec/lb) | 259.1 | 221.3 | 186.8 | 167.7 | 144.6 |

| metyl ethyl Ketare | 10 | 20 | 30 | 35 | 40 | 50 | 70 | 90 |
|---|---|---|---|---|---|---|---|---|
| TEFO | 90 | 80 | 70 | 65 | 60 | 50 | 30 | 10 |
| Const. Vol. T. (°K.)* | 4154 | 3032 | 2335 | 2166 | 2057 | 1867 | 1527 | 1145 |
| Const. Pre. T. (°K.)** | 3249 | 2407 | 1527 | 1380 | 1334 | 1258 | 1119 | 930 |
| Gas (moles/100 grs) | 3.829 | 4.573 | 5.333 | 5.300 | 5.174 | 4.902 | 4.326 | 3.785 |
| IMPETUS (ft-lb/lb) | 445821 | 385580 | 339034 | 316927 | 296880 | 254507 | 176527 | 114973 |
| Isp (lb-sec/.lb) | 258.0 | 232.2 | 207.3 | 202.0 | 197.5 | 188.5 | 168.4 | 143.3 |

*Chamber pressure at 50000 psi
**Chamber pressure at 1000 psi

TABLE VI

Diethyl Oxalate and TEFO Formulations

| Ingredient | | | | | | | | | |
|---|---|---|---|---|---|---|---|---|---|
| Diethyl Oxalate | 32 | 33 | 34 | 35 | 36 | 37 | 38 | 39 | 40 |
| TEFO | 68 | 67 | 66 | 65 | 64 | 63 | 62 | 61 | 60 |
| Const. Vol. T. (°K.) | 2697 | 2641 | 2574 | 2513 | 2457 | 2406 | 2360 | 2318 | 2278 |
| Const. Press. T. (°K.) | 2151 | 2081 | 2012 | 1943 | 1875 | 1807 | 1740 | 1673 | 1608 |
| Gas (moles/100 g) | 4.408 | 4.454 | 4.499 | 4.545 | 4.591 | 4.636 | 4.682 | 4.726 | 4.770 |
| IMPETUS (ft-lb.lb) | 330923 | 326820 | 321659 | 316988 | 312814 | 309073 | 305665 | 299421 | |
| Isp (lb-sec/lb) | 216.2 | 213.7 | 211.2 | 208.9 | 206.6 | 204.4 | 202.4 | 200.4 | 198.6 |

TABLE VII

Thermodynamic and Test Data on Fuels of This Invention

| | | | | | | | | |
|---|---|---|---|---|---|---|---|---|
| TEFO (% wt) | 67 | 64 | 70 | 65 | 65 | 65 | 70 | 65 |
| Diethyl Oxalate (% wt) | 33 | 36 | — | — | 17.5 | 25 | — | 20 |
| Methyl Ethylketone (% wt) | — | — | 30 | 35 | 17.5 | 10 | — | 15 |
| Acetone (% wt) | — | — | — | — | — | — | 30 | — |
| Const. Vol. T. (°K.) | 2641 | 2457 | 2335 | 2166 | — | 2353 | 2393 | 2304 |
| Const. Press. T. (°K.) | 2081 | 1875 | 1527 | 1380 | — | 1677 | 1661 | 1558 |
| Gas (moles/100 g) | 4.545 | 4.591 | 5.333 | 5.300 | — | 4.850 | 5.150 | 4.980 |
| Impetus (ft-lb.lb) | 326820 | 312814 | 339034 | 316929 | — | 318185 | 338127 | 319518 |
| Isp (lb-sec/lb) | 216.2 | 206.6 | 207.3 | 202.0 | — | 204.1 | 208.6 | 202.7 |
| H.O.E. (cal/g) | −845 | −803 | −816 | — | — | — | −848 | −760 |
| Cavity drop test (cm) (2 kg wt.) | 10.5 | 10.5 | 49 | — | — | — | 50 | 49 |
| Density (g/cc) (25° C.) | 1.308 | 1.368 | 1.247 | — | — | — | 1.257 | 1.301 |
| Exotherm T. (°C.) | 180 | 180 | 203 | — | — | — | 209 | 203 |
| TEFO ppt. (°C.) | —* | — | −30 | −25 | −45 | —* | —* | —* |

TABLE VIII

Acetone, Methylethyl ketone and TEFO Formulations

| Ingredient | | | | | |
|---|---|---|---|---|---|
| Acetone | 10 | 30 | 50 | 70 | 90 |
| TEFO | 90 | 70 | 50 | 30 | 10 |
| Const. Vol. T. (°K.)* | 4215 | 2393 | 1882 | 1543 | 1161 |
| Const. Pre. T. (°K.)** | 3275 | 1661 | 1258 | 1122 | 936 |
| Gas (moles/100 g) | 3.768 | 5.150 | 4.886 | 4.306 | 3.762 |
| Impetus (ft-lb/lb) | 446399 | 338127 | 259341 | 180262 | 116279 |
| Isp (lb-sec/lb) | 258.1 | 208.6 | 188.1 | 168.2 | 143.1 |
| Diethyl Oxalate | | 30 | 25 | 20 | |
| TEFO | | 65 | 65 | 65 | |
| Const. Vol. T. (°K.) | | 2424 | 2358 | 2304 | |
| Const. Press. T. (°K.) | | 1807 | 1677 | 1558 | |
| Gas (moles/100 grs) | | 4.698 | 4.850 | 4.980 | |
| Impetus (ft-lb/lb) | | 316916 | 318185 | 319518 | |
| Isp (lb-sec/.lb) | | 206.2 | 204.1 | 202.7 | |

What is claimed as new and desired to be secured by Letters Patent of the United States is:

1. A liquid fuel formulation comprising a mixture of from about 5 to 40% of a high energy ingredient selected from the group consisting of bis(2-fluoro-2,2-dinitroethyl)amine, bis(2-fluoro-2,2-dinitroethyl)formal and bis(2,2,2-trinitroethyl)formal, and
   from 60 to 95% of a mixture of propylene glycol dinitrate, 2-nitrodiphenylamine and di-n-butyl sebacate.

2. A liquid fuel formulation comprising a mixture of a high energy ingredient selected from the group consisting of bis(2-fluoro-2,2-dinitroethyl) amine, bis(2-fluoro-2,2-dinitroethyl) formal and bis(2,2,2-trinitroethyl) formal mixed with diethyl oxalate and methyl ethyl ketone.

3. The formulation of claim 2 wherein the amount of the high energy ingredient is in the range of 50 to 90%.

4. A liquid fuel composition comprising a mixture of propylene glycol dinitrate, 2 nitrodiphenylamine and di-n-butyl sebacate with bis (2,2,2-trinitroethyl) formal.

5. The composition of claim 4 wherein the amount of the bis (2,2,2-trinitroethyl) formal is within the range of 10% to 40% by weight.

6. A liquid fuel composition comprising a mixture of a high energy ingredient selected from the group consisting of bis (2-fluoro-2,2-dinitroethyl) amine, bis(2-fluoro-2,2-dinitroethyl) formal and bis(2,2,2-trinitroethyl) formal mixed with a small quantity of a melting point depressant selected from the group consisting acetone, methyl ethyl ketone and diethyl oxalate.

7. The liquid fuel formulation of claim 6 wherein the amount of the high energy ingredient varies between 30 and 90% of the mixture.

8. The liquid fuel of claim 6 wherein the amount of the melting point depressant varies between 10 and 30% by weight of the total mixture.

* * * * *